United States Patent
Zhang et al.

(10) Patent No.: US 10,329,316 B2
(45) Date of Patent: Jun. 25, 2019

(54) PHENYLPROPANOID COMPOUND AND PREPARATION METHOD AND USE THEREOF

(71) Applicant: QIANJIN PHARMACEUTICAL CO., LTD., Hunan (CN)

(72) Inventors: Peng Zhang, Hunan (CN); Kaifeng Peng, Hunan (CN); Yun Gong, Hunan (CN); Fujun Li, Hunan (CN); Nifu Liu, Hunan (CN); Bohou Xia, Hunan (CN); Limei Lin, Hunan (CN)

(73) Assignee: QIANJIN PHARMACEUTICAL CO., LTD., Hunan (CN)

( * ) Notice: Subject to any disclaimer, the term of this patent is extended or adjusted under 35 U.S.C. 154(b) by 0 days.

(21) Appl. No.: 16/132,506

(22) Filed: Sep. 17, 2018

(65) Prior Publication Data

US 2019/0016744 A1    Jan. 17, 2019

Related U.S. Application Data

(63) Continuation-in-part of application No. PCT/CN2017/076455, filed on Mar. 13, 2017.

(30) Foreign Application Priority Data

Mar. 17, 2016   (CN) .......................... 2016 1 0154676
Mar. 17, 2016   (CN) .......................... 2016 1 0154680
Mar. 17, 2016   (CN) .......................... 2016 1 0154851

(51) Int. Cl.
*A61K 31/7034*   (2006.01)
*C07H 15/203*   (2006.01)
(Continued)

(52) U.S. Cl.
CPC ....... *C07H 15/203* (2013.01); *A61K 31/7034* (2013.01); *A61K 36/19* (2013.01);
(Continued)

(58) Field of Classification Search
None
See application file for complete search history.

(56) References Cited

FOREIGN PATENT DOCUMENTS

CN   1078079   1/2002
CN   1158087   7/2004
(Continued)

OTHER PUBLICATIONS

Wang et al., "Antioxidant phenolic constituents from Fagopyrum dibotrys," Journal of Ethnopharmacology, vol. 99, Apr. 7, 2005, pp. 259-264.

(Continued)

*Primary Examiner* — Traviss C McIntosh, III
(74) *Attorney, Agent, or Firm* — JCIPRNET

(57) ABSTRACT

The present invention provides a phenylpropanoid compound and a preparation method and use thereof. The phenylpropanoid compound has a structural formula shown as formula (I), and the pharmaceutically acceptable salt has a structural formula shown as formula (II), formula (III), formula (IV), or formula (V). The phenylpropanoid compound and the pharmaceutically acceptable salt thereof have an effect on inhibiting a content of an inflammatory cytokine NO and an expression of an inflammatory cytokine TNF-α, have an effect on inhibiting a hydroxyl radical (—OH), thereby have anti-inflammatory and antioxidant activities, and has a good application prospect in preparing of a medicine for treating an inflammatory disease related to the above factors, such as cervicitis, endometritis, pelvic inflammatory disease, mastitis, sphagitis and/or arthritis.

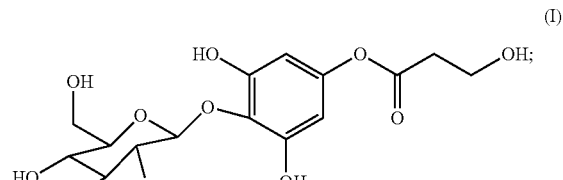

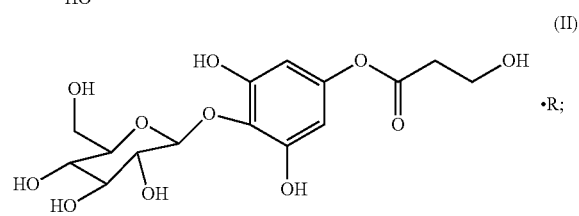

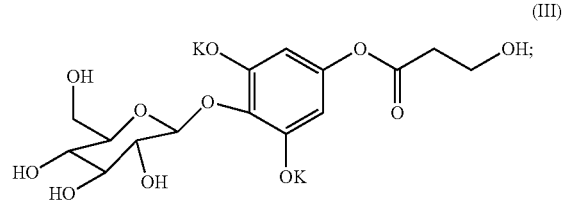

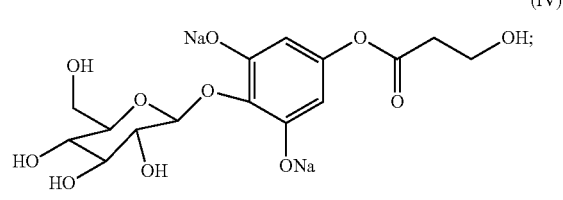

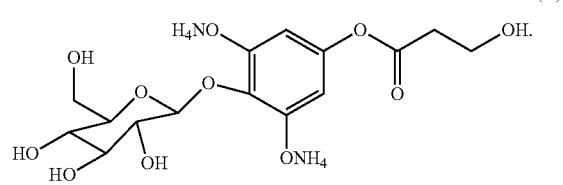

20 Claims, 3 Drawing Sheets

(51) Int. Cl.
*A61K 36/758* (2006.01)
*A61K 36/19* (2006.01)
*A61K 36/29* (2006.01)
*A61K 36/486* (2006.01)
*A61K 36/738* (2006.01)
*A61P 29/00* (2006.01)
*A61K 36/232* (2006.01)
*A61K 36/28* (2006.01)
*A61K 36/48* (2006.01)
*C07H 1/08* (2006.01)
*A61K 45/06* (2006.01)
*A61K 9/00* (2006.01)
*A61K 9/16* (2006.01)
*A61K 9/20* (2006.01)
*A61K 9/48* (2006.01)

(52) U.S. Cl.
CPC ............ *A61K 36/232* (2013.01); *A61K 36/28* (2013.01); *A61K 36/29* (2013.01); *A61K 36/48* (2013.01); *A61K 36/486* (2013.01); *A61K 36/738* (2013.01); *A61K 36/758* (2013.01); *A61K 45/06* (2013.01); *A61P 29/00* (2018.01); *C07H 1/08* (2013.01); *A61K 9/0019* (2013.01); *A61K 9/16* (2013.01); *A61K 9/20* (2013.01); *A61K 9/48* (2013.01); *A61K 2300/00* (2013.01)

(56) References Cited

FOREIGN PATENT DOCUMENTS

| | | |
|---|---|---|
| CN | 1170549 | 10/2004 |
| CN | 1296071 | 1/2007 |
| CN | 1296072 | 1/2007 |
| CN | 1296073 | 1/2007 |
| CN | 1321631 | 6/2007 |
| CN | 1330335 | 8/2007 |
| CN | 101058594 | 10/2007 |
| CN | 101235059 | 8/2008 |
| CN | 101538272 | 9/2009 |
| CN | 105708845 | 6/2016 |
| CN | 105732736 | 7/2016 |
| CN | 105777821 | 7/2016 |
| WO | 03101446 | 12/2003 |

OTHER PUBLICATIONS

Kuo et al., "Cytotoxic Phenylpropanoid Glycosides from the Stems of Smilax china," J. Nat. Prod., vol. 68, Oct. 6, 2005, pp. 1475-1478.

PHENYLPROPANOID COMPOUND AND PREPARATION METHOD AND USE THEREOF

CROSS-REFERENCE TO RELATED APPLICATION

This is a continuation-in-part application of International Application No. PCT/CN2017/076455, filed on Mar. 13, 2017, which claims the priority benefits of China Application No. 201610154851.0, filed on Mar. 17, 2016, China Application No. 201610154680.1, filed on Mar. 17, 2016, and China Application No. 201610154676.5, filed on Mar. 17, 2016. The entirety of each of the above-mentioned patent applications is hereby incorporated by reference herein and made a part of this specification.

BACKGROUND

Technical Field

The present invention relates to the technical field of medicine, and more particularly, to a phenylpropanoid compound and a preparation method and use thereof.

Related Art

Constituent structures extracted from natural medicines are diverse and has significant activities, and their separation, purification, structural modification, transformation and total synthesis have always been a major idea for developing new medicines.

TNF-α: is a cytokine that can directly kill tumor cells without significant toxicity to normal cells; and it is one of the most active bioactive factors found to directly kill tumors so far, but its toxic side effects are also very serious.

IL-1β: synergistically stimulates APC and T cell activation at a locally low concentration, promotes B cell proliferation and secretion of antibodies, and regulates immune secretion; and endocrine effect occurs when it is produced in large quantities: inducing acute-phase protein synthesis in liver, causing fever and cachexia.

IL-6: human IL-6 gene is located on chromosome 7; IL-6 has a molecular weight between 21 and 30 KD; it is mainly produced by mononuclear macrophages, Th2 cells, vascular endothelial cells, and fibroblasts; and it is able to stimulate and activate B cell proliferation and secretion of antibodies, to stimulate T cell proliferation and CTL activation, to stimulate liver cells to synthesize acute-phase proteins, participate in inflammatory response, and to promote development of blood cells.

IL-6 can be synthesized by a plurality of cells, including activated T cells and B cells, mononuclear macrophages, endothelial cells, epithelial cells, and fibroblasts. IL-6 acts on many target cells, including macrophages, hepatocytes, dormant T cells, activated B cells and plasma cells; and their biological effects are also very complex.

OH is the most active reactive oxygen species in biological systems, which can cause oxidative damage to DNA, proteins and lipids in cells and organisms.

Macrophages can produce a plurality of inflammatory mediators to be involved in the inflammatory response, in which NO is an important inflammatory cytokine. NO is involved in various physiological and pathological processes, and excessive NO will promote occurrence and development of inflammatory diseases, and can also induce other inflammatory factors.

Therefore, it is very necessary to seek a new preparation method to separate a new compound from a natural plant to inhibit a content of the inflammatory cytokine NO, to inhibit an expression of the inflammatory cytokine TNF-α, to inhibit an activity of a hydroxyl radical (—OH), and to apply to treatment of an inflammatory disease.

A medicinal material, Radix Et *Caulis Flemingiae*, is a dried root of a plant *Moghania macrophylla* (Willd.) O. Kuntze of Flemingl.Roxb. or *Moghania* of Leguminosae, which is mainly distributed in the southeast of China. Radix Et *Caulis Flemingiae* is a local medicinal material in Guangxi, and has a wide range of folk medicine foundation. It is sweet, slightly sputum, natured, and has effects such as heat clearing and dehumidification, mainly used to treat rheumatic bone pain, traumatic injury, chronic nephritis, and gynecologic diseases such as dysmenorrhea and leucorrhea overmuch.

Reported constituents of *Moghania macrophylla* (Willd.) O. Kuntze mainly include flavonoids, steroids, terpenoids, anthraquinones, and volatile oils, all of which have certain pharmacological activities, and their pharmacological activities are diverse, and are reported to have neuroprotective effects, anti-inflammatory, anti-oxidative effects, anthelmintic effects on pathogenic microorganisms, hormonal effects, cytotoxicity, antibacterial effects, immune enhancement effects, and anti-fatigue effects.

At present, Radix Et *Caulis Flemingiae* is widely used in producing traditional Chinese medicines for gynecology, rheumatic arthralgia and etc., such as gynecologic Qianjin tablets, gynecologic Qianjin capsules, Jinji granules, Jinji capsules, and etc. These traditional Chinese medicines are mainly used for gynecological diseases (dysmenorrhea, uterine cold infertility, hysteroptosis, pelvic inflammatory disease, mastitis, leucorrhea overmuch, postpartum blood deficiency, joint pain, postpartum waist-knee pain, hypogalactia and breast sore, and etc.), and weakness anemia (women's anemia, vital energy and blood weakness and post-ill vital energy debility, and etc.). In recent years, the gynecologic Qianjin tablets are more clinically reported in the effects on treatment of gynecologic inflammation.

At present, in the literatures of Radix Et *Caulis Flemingiae*, there are few reports on phenylpropanoid compound, and thus it is of great significance to seek a new effective phenylpropanoid compound and a preparation method thereof, to perform separation, purification, structural modification and synthesis for the compound, to develop a new medicine, and to apply to treatment of inflammatory diseases.

SUMMARY OF THE INVENTION

One technical problem to be solved by the present invention is to provide a new phenylpropanoid compound and a pharmaceutically acceptable salt thereof.

Another technical problem to be solved by the present invention is to provide a pharmaceutical composition of the phenylpropanoid compound and/or the pharmaceutically acceptable salt.

Another technical problem to be solved by the present invention is to provide a preparation method of separating and obtaining the phenylpropanoid compound from a dried root of *Moghania macrophylla* (Willd.) O. Kuntze. The phenylpropanoid compound obtained by extraction and separation by this preparation method can inhibit an expression of an inflammatory cytokine NO and an expression of inflammatory cytokine TNF-α, and has an inhibitory effect on a hydroxyl radical (—OH), thereby having anti-inflammatory and antioxidant activities, which is beneficial for treatment of various inflammatory diseases. The phenylpropanoid compound can be developed into a new medicine.

An objective of the present invention is to provide a phenylpropanoid compound for medical use.

The objective of the present invention is realized by the following technical solution:

a phenylpropanoid compound and a pharmaceutically acceptable salt thereof is provided, the phenylpropanoid compound has a structural formula shown as formula (I), and the pharmaceutically acceptable salt has a structural formula shown as formula (II), formula (III), formula (IV), or formula (V):

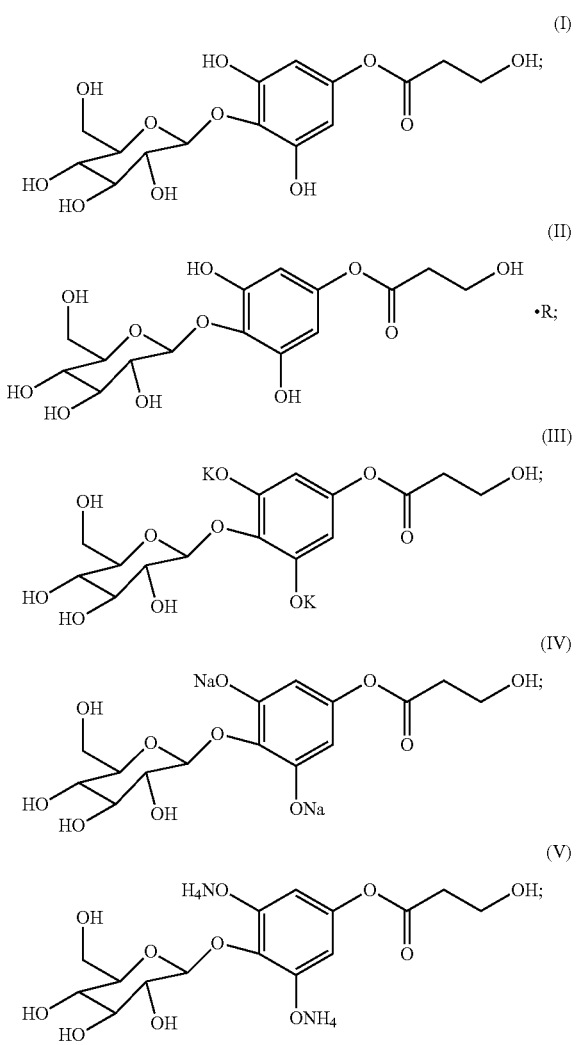

wherein the R is an inorganic acid.

Preferably, the inorganic acid is selected from a group consisting of hydrochloric acid, hydrobromic acid, hydrofluoric acid, hydroiodic acid, sulfuric acid and phosphoric acid.

Preferably, the pharmaceutically acceptable salt is an ammonium salt.

Simultaneously, the present invention provides a pharmaceutical composition, and the pharmaceutical composition contains the phenylpropanoid compound shown as the formula (I) and/or pharmaceutically acceptable salt thereof.

Preferably, the pharmaceutical composition contains the phenylpropanoid compound shown as the formula (I) and/or pharmaceutically acceptable salt thereof, as well as a pharmaceutically permissible supplementary material and/or carrier.

Preferably, the pharmaceutical composition contains the phenylpropanoid compound shown as the formula (I) and/or pharmaceutically acceptable salt thereof, as well as other medicinal ingredients.

Preferably, the pharmaceutical composition further contains one or more of Radix *Rosa Laevigata*, *Zanthoxylum dissitum* Hemsl., *Caulis Spatholobi*, *Caulis Mahoniae*, *Herba Andrographis*, Radix *Angelicae Sinensis*, Radix *Codonopsis*.

Preferably, the pharmaceutical composition further contains an extract of one or more of Radix *Rosa Laevigata*, *Zanthoxylum dissitum* Hemsl., *Caulis Spatholobi*, *Caulis Mahoniae*, *Herba Andrographis*, Radix *Angelicae Sinensis*, Radix *Codonopsis*.

The extract is prepared by the extraction method described in any one or several patent documents of Patent Publication No. CN1078079C, CN1170549C, CN1158087C, CN1330335C, CN1296071C, CN1321631C, CN1296072C, CN1296073C.

The pharmaceutical composition may have a Rhin selected from a group consisting of a tablet, a capsule, a powder, a granule, a pill, a solution, a suspension, a syrup, an injection, an ointment, a suppository and a spray, as well as other forms achievable in the prior art.

The phenylpropanoid compound and the pharmaceutically acceptable salt thereof have an effect on inhibiting the expression of the inflammatory cytokine NO and the expression of the inflammatory cytokine TNF-α, have an effect on inhibiting the hydroxyl radical (—OH), thereby have anti-inflammatory and antioxidant activities, and can be applied for the preparation of a medicine for treating an inflammatory disease, including but not limited to cervicitis, endometritis, pelvic inflammatory disease, mastitis, sphagitis and/or arthritis, and etc.

The objective of the present invention is to obtain a new compound from the traditional Chinese medicine prescription by solvent extraction, column chromatography separation, preparative liquid phase separation and purification from the prescription of gynecological Qianjin tablets and gynecological Qianjin capsules. Experiments have confirmed that it can be applied to the treatment of inflammatory diseases such as cervicitis, endometritis, pelvic inflammatory disease, mastitis, sphagitis and/or arthritis.

Specifically, by selecting the dried root of *Moghania macrophylla* (Willd.) O. Kuntze from the prescription of gynecological Qianjin tablets and gynecological Qianjin capsules, the inventors obtain the phenylpropanoid compound according to the present invention by solvent extraction, column chromatography separation, preparative liquid phase separation and purification, and the compound is then subjected to a cell test to determine the degree of inhibition of the inflammatory cytokine NO, TNF-α and hydroxyl radical (—OH). Experiments shows that the phenylpropanoid compound has a significant effect on inhibiting the increase of NO content induced by LPS in a concentration range of 6.88 to 12.38 µg/mL, and shows a dose-dependent relationship. Within the concentration range of 6.88 to 12.38 µg/mL, it can significantly inhibit the production of TNF-α in Raw 264.7 cells (p<0.05), and shows a significant dose-dependent relationship. The phenylpropanoid compound has a significant effect on inhibiting the increase of OH induced by LPS in a concentration range of 4.13 to 12.38 μg/mL, and shows a dose-dependent relationship.

The preparation method of the phenylpropanoid compound according to the present invention comprises following steps:

S1, taking a root of *Moghania macrophylla* (Willd.) O. Kuntze as a raw material, drying, stripping and slicing, extracting with an ethanol solution to obtain an extracted solution, merging the extracted solution, concentrating till no alcohol taste, obtaining an extractum for future use;

S2, dissolving the extractum obtained in the step S1 with water, eluting the dissolved extractum by a macroporous adsorption resin column, with an eluent being an ethanol-water system, collecting first three column volumes of an eluate, naming the eluate as MM-1, for future use;

S3, eluting a fraction MM-1 collected in the step S2 by a reverse phase material ODS column chromatography, with an eluent being the ethanol-water system, eluting for 18 column volumes, collecting one fraction of eluate per three column volumes, thereby collecting 6 fractions in order, naming the 6 fractions as MM-11, MM-12, MM-13, MM-14, MM-15, MM-16 respectively, for future use;

S4, separating the fraction MM-12 collected in the step S3 by a preparative liquid phase, with a mobile phase being a methanol-water-acetic acid system, collecting eluates in peak-order, collecting 7 fractions in total, naming the 7 fractions as MM-121, MM-122, MM-123, MM-124, MM-125, MM-126, MM-127 respectively, for future use; and S5, purifying the fraction MM-125 collected in the step S4 by the preparative liquid phase, with a mobile phase being the methanol-water-acetic acid system, collecting an eluate, obtaining the phenylpropanoid compound after recrystallizing. The phenylpropanoid compound has a purity of 99.84%. The structural formula of the phenylpropanoid compound is shown in the formula (I):

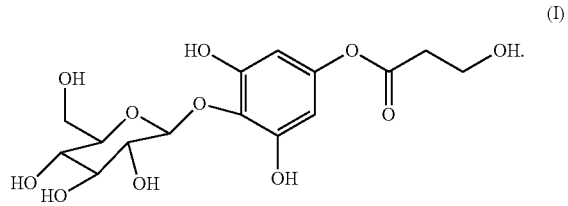 [SMILES: O=C(CCO)Oc1cc(O)c(OC2OC(CO)C(O)C(O)C2O)c(O)c1]

(I)

Preferably, in the step S1, a concentration of the ethanol solution is 50 to 80% by volume, and preferably the concentration of the ethanol solution is 60% by volume.

Preferably, in the step S1, extracting with ethanol performs 2 to 4 times, and each time is 1 to 3 hours, preferably extracting with ethanol performs 3 times, and each time is 2 hours.

Preferably, in the step S2, the macroporous adsorption resin adopts a D101 macroporous adsorption resin.

Preferably, in the step S2, a volume ratio of ethanol to water is 0:100 to 15:85.

Preferably, in the step S3, a volume ratio of methanol to water is 20:80 to 30:70, preferably 25:75.

Preferably, in the step S4, a volume ratio of methanol to water to acetic acid is 10:90:0.01 to 35:65:0.01, preferably 15:85:0.01.

Preferably, in the step S4, a chromatographic column of the preparative liquid phase is YMC, 20 mm*250 mm, and a flow rate of the mobile phase is 5 to 10 mL/min, and preferably the flow rate is 5 mL/min.

Preferably, in the step S5, a volume ratio of methanol to water to acetic acid is 15:85:0.01.

Preferably, in the step S5, a chromatographic column of the preparative liquid phase is YMC, 20 mm*250 mm, and a flow rate of the mobile phase is 5 mL/min.

The present invention provides the phenylpropanoid compound prepared by the preparation method.

Use of the phenylpropanoid compound and the pharmaceutically acceptable salt thereof in preparing a medicine for treating an inflammatory disease is provided.

Preferably, use of the phenylpropanoid compound and the pharmaceutically acceptable salt thereof in preparing a medicine for inhibiting a content of an inflammatory cytokine NO or inhibiting an expression of an inflammatory cytokine TNF-α or inhibiting an activity of a hydroxyl radical, used in the medicine for treating the inflammatory disease.

Preferably, the inflammatory disease is cervicitis, endometritis, pelvic inflammatory disease, mastitis, sphagitis and/or arthritis.

The medicine contains the pharmaceutically permissible supplementary material and/or carrier.

Preferably, the medicine further contains other medicinal ingredients.

Preferably, the medicine further contains one or more of Radix *Rosa Laevigata*, *Zanthoxylum dissitum* Hemsl., *Caulis Spatholobi*, *Caulis Mahoniae*, *Herba Andrographis*, Radix *Angelicae Sinensis*, Radix *Codonopsis*. Preferably, the medicine further contains an extract of one or more of Radix *Rosa Laevigata*, *Zanthoxylum dissitum* Hemsl., *Caulis Spatholobi*, *Caulis Mahoniae*, *Herba Andrographis*, Radix *Angelicae Sinensis*, Radix *Codonopsis*.

Preferably, the medicine has a form selected from a group consisting of a tablet, a capsule, a powder, a granule, a pill, a solution, a suspension, a syrup, an injection, an ointment, a suppository and a spray.

The beneficial effects of the present invention are as follows:

The present invention provides a novel phenylpropanoid compound, and meanwhile provides a pharmaceutically acceptable salt of the phenylpropanoid compound. The phenylpropanoid compound or the pharmaceutically acceptable salt thereof can inhibit a content of an inflammatory cytokine NO, inhibit an expression effect of an inflammatory cytokine TNF-α, have an inhibiting effect on a hydroxyl radical (—OH), thus possess anti-inflammatory and antioxidation activity and be well used for preparing a medicine for treating an inflammatory disease, including but not limited to medicines for treating inflammatory diseases such as cervicitis, endometritis, pelvic inflammatory disease, mastitis, sphagitis and/or arthritis, and providing a strong technical base for development of anti-inflammatory medicines.

The present invention provides a preparation method of the novel phenylpropanoid compound and the pharmaceutically acceptable salt thereof, and isolates a novel phenylpropanoid compound from a dried root of *Moghania macrophylla* (Willd.) O. Kuntze for the first time. The compounds prepared can inhibit a content of the inflammatory cytokine NO and an expression effect of the inflammatory cytokine TNF-α, have an inhibiting effect on the hydroxyl radical (—OH), thus possess anti-inflammatory and antioxidation activity and be used for medicines for treating inflammatory diseases such as cervicitis, endometritis, pelvic inflammatory disease, mastitis, sphagitis and/or arthritis.

A purpose of the present invention is to prepare a novel phenylpropanoid compound by solvent extraction, column chromatography isolation, preparative liquid phase isolation and purification from conventional prescriptions of traditional Chinese medicine and prescriptions of Gynecologic Qianjin Tablets and Gynecologic Qianjin Capsules. It has been confirmed from experiments that the phenylpropanoid compound can be used for inflammatory diseases, for example treating diseases such as cervicitis, endometritis, pelvic inflammatory disease, mastitis, sphagitis and/or arthritis.

Particularly, from the prescriptions of Gynecologic Qianjin Tablets and Gynecologic Qianjin Capsules, the inventors obtain the phenylpropanoid compound of the present invention by scientifically selecting the dried root of the *Moghania macrophylla* (Willd.) O. Kuntze and carrying out solvent extraction, column chromatography isolation, preparative liquid phase isolation and purification, then carry out a cell assay on the compounds and determine inhibition degrees of the phenylpropanoid compound on the inflammatory cytokine NO, the inflammatory cytokine TNF-α and the hydroxyl radical (—OH). It is shown from experiments that the compounds within a concentration range (6.88 to 12.38 mg/mL) possess remarkable inhibition effect on the increasing content of NO caused by LPS, and show a remarkable dose-dependence relationship. Within the concentration rage (6.88 to 12.38 µg/mL), the compounds can significantly inhibit cell Raw 264.7 from generating the inflammatory cytokine TNF-α ($p<0.05$), and show a remarkable dose-dependence relationship. Within the concentration rage (4.13 to 12.38 µg/mL), the compounds possess remarkable inhibition effect on the increasing content of OH caused by LPS, and show a certain dose-dependence relationship.

The present invention provides a novel phenylpropanoid compound with a simple structure and a high purity, and the isolation method thereof is simple and convenient with easy synthesis, being suitable for industrialization of new medicine.

DESCRIPTION OF THE EMBODIMENTS

Figure 1:
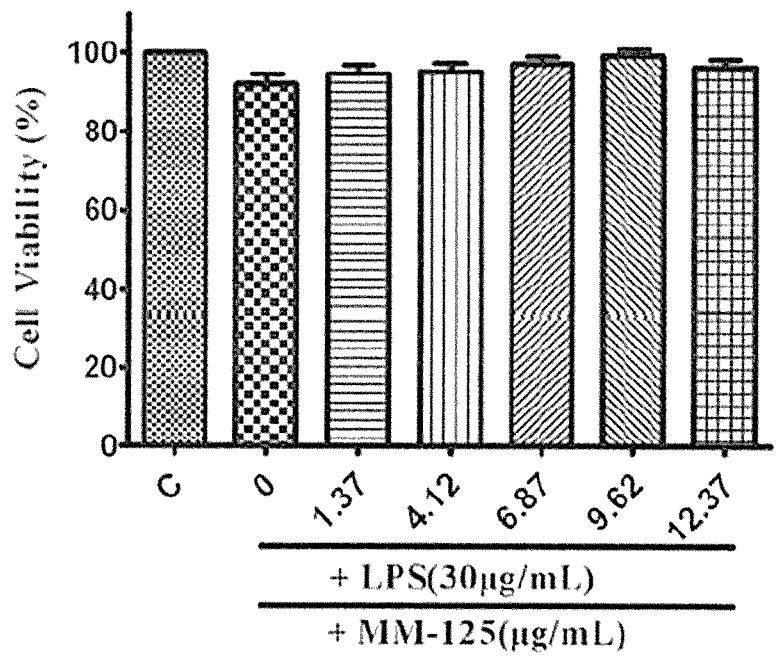
FIG. 1 shows an effect diagram of the phenylpropanoid compound of the present invention on cell viability.

The present invention is further described below in combination with the accompanied drawings and specific embodiments, but the embodiments do not limit the present invention in any forms. Unless specified, reagents, methods and equipment used in the present invention are conventional reagents, methods and equipment used in the art. Unless specified, raw materials and equipment used in the present invention are commercially available conventional raw materials and equipment used in the art.

The compounds of the present invention are a phenylpropanoid compound shown as formula (I) and a pharmaceutically acceptable salt thereof shown as formula (II) or formula (III). The compounds can be prepared by a method of extracting a raw material *Moghania macrophylla* (Willd.) O. Kuntze, which the method is provided by the present invention, and also can be prepared by methods such as in combination with chemical synthesis in the art according to a structural formula provided by the present invention.

As the salts of the phenylpropanoid compound of the present invention, they only need to be the pharmaceutically acceptable salts, listed as inorganic salts generated by the phenylpropanoid compound with inorganic acids such as hydrochloric acid, hydrobromic acid, hydrofluoric acid, hydroiodic acid, sulfuric acid, nitric acid, carboxylic acid, phosphoric acid, lactic acid and the like; sulfonate generated by the phenylpropanoid compound with sulfonic acid; alkali metal salts generated by the phenylpropanoid compound with hydroxides of alkali metals such as potassium, sodium, calcium, magnesium, lithium and the like; and ammonium salts generated by the phenylpropanoid compound with ammoniums.

The phenylpropanoid compound of the present invention can be used for a medicine for treating inflammatory diseases such as cervicitis, endometritis, pelvic inflammatory disease, mastitis, sphagitis and/or arthritis and the like.

The compound of the present invention can be used as a pharmaceutical composition with a pharmaceutically permissible supplementary material and/or carrier, and also can be used as a pharmaceutical composition with a group of one or more of Radix *Rosa Laevigata*, *Zanthoxylum dissitum* Hemsl., *Caulis Spatholobi*, *Caulis Mahoniae*, *Herba Andrographis*, Radix *Angelicae Sinensis*, Radix *Codonopsis*, or an extract thereof under the condition of adding the pharmaceutically permissible supplementary material and/or carrier. The compound of the present invention can also be used as a pharmaceutical composition with other pharmaceutically permissible medicinal ingredients.

As the pharmaceutical composition, it can have a form such as a tablet, a capsule, a powder, a granule, a pill, a solution, a suspension, a syrup, an injection, an ointment, a suppository, a spray and the like.

Further, the tablet can be prepared to a sugarcoated tablet, a film-coated tablet, an enteric coated tablet or a double-layer tablet or a multi-layer tablet, under the condition of adding the pharmaceutically permissible supplementary material and/or carrier.

The supplementary material and/or carrier of the present invention can be prepared into follows:

a solid formulation, that is, an additive can be used, for example, sucrose, lactose, cellulosic saccharide, maltitol, glucose, starches, agar, alginates, chitin, chitosans, pectins, arabic gums, gelatins, collagens, casein, albumin, calcium phosphate, sorbitol, glycine, glycerol, polyethylene glycol, sodium bicarbonate, talc and the like;

a semisolid formulation, that is, animal and vegetable oils (olive oil, corn oil, castor oil, etc.), mineral oils (Vaseline, white petrolatum, solid paraffin, etc.), waxes (jojoba oil, carnauba wax, beeswax, etc.), partially synthetic or fully synthetic glycerol fatty acid esters (lauric acid, myristic acid, palmitic acid, etc.) and the like can be used;

a liquid formulation, that is, an additive can be used, for example, sodium chloride, glucose, sorbitol, glycerol, olive oil, propylene glycol, ethanol and the like. Especially under the condition of preparing into an injection, that is, sterile aqueous solution can be used, for example, physiological saline, isotonic solution and oily liquid, such as sesame oil and soybean oil. Besides, a suitable suspending agent can be used simultaneously according to needs, for example, sodium carboxymethyl cellulose, nonionic surfactant and cosolvent, such as benzyl benzoate and benzyl alcohol.

A content of active ingredients in these formulations is 0.01 to 80 wt % of the formulation, suitably 1 to 50 wt %, and a dosage varies according to differences in symptom, body weight, age of a patient.

Example 1

Preparation of a Phenylpropanoid Compound

The present example provides a preparation method of the phenylpropanoid compound shown as formula (I), comprising steps as follows:

S1, taking 50 kg of *Moghania macrophylla* (Willd.) O. Kuntze, with a root as a raw material, drying, stripping and slicing into small pieces, carrying out a reflux extraction with 8 multiples of 60% ethanol in 3 times while 2 hours for each time to obtain an extracted solution, merging the extracted solution, concentrating till no alcohol taste, obtaining an extractum for future use;

S2, dissolving the extractum after concentration obtained in the step S1 with 10 L of water, eluting the dissolved extractum by D101 macroporous adsorption resin column, with an eluent being water for three column volumes, collecting an eluate, naming the eluate as MM-1, for future use;

S3, eluting a fraction MM-1 collected in the step S2 by a reverse phase material ODS column chromatography, with an eluent being the ethanol-water system in a volume ratio of 25:75, eluting for 18 column volumes, collecting one fraction of eluate per three column volumes, thereby collecting 6 fractions in order, naming the 6 fractions as MM-11, MM-12, MM-13, MM-14, MM-15, MM-16 respectively, for future use; S4, separating the fraction MM-12 collected in the step S3 by a preparative liquid phase, with a chromatographic column for the preparative liquid phase being YMC of 20 mm*250 mm with a velocity of 5 ml/min, a mobile phase being a methanol-water-acetic acid system, and a volume ratio of methanol-water-acetic acid being 25:75:0.01, collecting eluates in peak-order, collecting 7 fractions in total, naming the 7 fractions as MM-121, MM-122, MM-123, MM-124, MM-125, MM-126, MM-127 respectively, for future use; and S5, purifying the fraction MM-125 collected in the step S4 by the preparative liquid phase, with a chromatographic column for the preparative liquid phase being YMC of 20 mm*250 mm with a velocity of 5 ml/min, a mobile phase being the methanol-water-acetic acid system, and a volume ratio of methanol-water-acetic acid being 15:85:0.01, collecting an eluate, obtaining the phenylpropanoid compound after recrystallizing.

Example 2

Preparation of a Phenylpropanoid Compound

The present example provides a preparation method of the phenylpropanoid compound shown as formula (I), comprising steps as follows:

S1, taking 40 kg of *Moghania macrophylla* (Willd.) O. Kuntze, with a root as a raw material, drying, stripping and slicing into small pieces, carrying out a reflux extraction with 6 multiples of 50% ethanol in 2 times while 1 hour for each time to obtain an extracted solution, merging the extracted solution, concentrating till no alcohol taste, obtaining an extractum for future use;

S2, dissolving the extractum after concentration obtained in the step S1 with 5 L of water, eluting the dissolved extractum by D101 macroporous adsorption resin column, with an eluent being ethanol and water in a volume ratio of 15:85 for three column volumes, collecting an eluate, naming the eluate as MM-1, for future use;

S3, eluting a fraction MM-1 collected in the step S2 by a reverse phase material ODS column chromatography, with an eluent being the ethanol-water system in a volume ratio of 25:80, eluting for 18 column volumes, collecting one fraction of eluate per three column volumes, thereby collecting 6 fractions in order, naming the 6 fractions as MM-11, MM-12, MM-13, MM-14, MM-15, MM-16 respectively, for future use;

S4, separating the fraction MM-12 collected in the step S3 by a preparative liquid phase, with a chromatographic column for the preparative liquid phase being YMC of 20 mm*250 mm with a velocity of 10 ml/min, a mobile phase being a methanol-water-acetic acid system, and a volume ratio of methanol-water-acetic acid being 35:65:0.01, collecting eluates in peak-order, collecting 7 fractions in total, naming the 7 fractions as MM-121, MM-122, MM-123, MM-124, MM-125, MM-126, MM-127 respectively, for future use; and S5, purifying the fraction MM-125 collected in the step S4 by the preparative liquid phase, with a chromatographic column for the preparative liquid phase being YMC of 20 mm*250 mm with a velocity of 5 ml/min, a mobile phase being the methanol-water-acetic acid system, and a volume ratio of methanol-water-acetic acid being 15:85:0.01, collecting an eluate, obtaining the phenylpropanoid compound after recrystallizing.

Example 3

Preparation of a Phenylpropanoid Compound

The present example provides a preparation method of the phenylpropanoid compound shown as formula (I), comprising steps as follows:

S1, taking 60 kg of *Moghania macrophylla* (Willd.) O. Kuntze, with a root as a raw material, drying, stripping and slicing into small pieces, carrying out a reflux extraction with 7 multiples of 70% ethanol in 4 times while 3 hours for each time to obtain an extracted solution, merging the extracted solution, concentrating till no alcohol taste, obtaining an extractum for future use;

S2, dissolving the extractum after concentration obtained in the step S1 with 8 L of water, eluting the dissolved extractum by D101 macroporous adsorption resin column, with an eluent being ethanol and water in a volume ratio of 10:90 for three column volumes, collecting an eluate, naming the eluate as MM-1, for future use;

S3, eluting a fraction MM-1 collected in the step S2 by a reverse phase material ODS column chromatography, with an eluent being the ethanol-water system in a volume ratio of 30:70, eluting for 18 column volumes, collecting one fraction of eluate per three column volumes, thereby collecting 6 fractions in order, naming the 6 fractions as MM-11, MM-12, MM-13, MM-14, MM-15, MM-16 respectively, for future use;

S4, separating the faction MM-12 collected in the step S3 by a preparative liquid phase, with a chromatographic column for the preparative liquid phase being YMC of 20 mm*250 mm with a velocity of 10 ml/min, a mobile phase being a methanol-water-acetic acid system, and a volume ratio of methanol-water-acetic acid being 30:70:0.01, collecting eluates in peak-order, collecting 7 fractions in total, naming the 7 fractions as MM-121, MM-122, MM-123, MM-124, MM-125, MM-126, MM-127 respectively, for future use; and S5, purifying the fraction MM-125 collected in the step S4 by the preparative liquid phase, with a chromatographic column for the preparative liquid phase being YMC of 20 mm*250 mm with a velocity of 5 ml/min, a mobile phase being the methanol-water-acetic acid system, and a volume ratio of methanol-water-acetic acid being 15:85:0.01, collecting an eluate, obtaining the phenylpropanoid compound after recrystallizing.

Example 4

Preparation of a Phenylpropanoid Compound

The present example provides a preparation method of the phenylpropanoid compound shown as formula (I), comprising steps as follows:

S1, taking 50 kg of *Moghania macrophylla* (Willd.) O. Kuntze, with a root as a raw material, drying, stripping and slicing into small pieces, carrying out a reflux extraction with 8 multiples of 60% ethanol in 2 times while 1.5 hours for each time to obtain an extracted solution, merging the extracted solution, concentrating till no alcohol taste, obtaining an extractum for future use;

S2, dissolving the extractum after concentration obtained in the step S1 with 6 L of water, eluting the dissolved extractum by D101 macroporous adsorption resin column, with an eluent being ethanol and water in a volume ratio of 5:95 for three column volumes, collecting an eluate, naming the eluate as MM-1, for future use;

S3, eluting a fraction MM-1 collected in the step S2 by a reverse phase material ODS column chromatography, with an eluent being the ethanol-water system in a volume ratio of 25:75, eluting for 18 column volumes, collecting one fraction of eluate per three column volumes, thereby collecting 6 fractions in order, naming the 6 fractions as MM-11, MM-12, MM-13, MM-14, MM-15, MM-16 respectively, for future use;

S4, separating the fraction MM-12 collected in the step S3 by a preparative liquid phase, with a chromatographic column for the preparative liquid phase being YMC of 20 mm*250 mm with a velocity of 10 ml/min, a mobile phase being a methanol-water-acetic acid system, and a volume ratio of methanol-water-acetic acid being 25:75:0.01, collecting eluates in peak-order, collecting 7 fractions in total, naming the 7 fractions as MM-121, MM-122, MM-123, MM-124, MM-125, MM-126, MM-127 respectively, for future use; and S5, purifying the fraction MM-125 collected in the step S4 by the preparative liquid phase, with a chromatographic column for the preparative liquid phase being YMC of 20 mm*250 mm with a velocity of 5 ml/min, a mobile phase being the methanol-water-acetic acid system, and a volume ratio of methanol-water-acetic acid being 15:85:0.01, collecting an eluate, obtaining the phenylpropanoid compound after recrystallizing.

Example 5

Preparation of a Phenylpropanoid Compound

The present example provides a preparation method of the phenylpropanoid compound shown as formula (I), comprising steps as follows:

S1, taking 50 kg of *Moghania macrophylla* (Willd.) O. Kuntze, with a root as a raw material, drying, stripping and slicing into small pieces, carrying out a reflux extraction with 8 multiples of 80% ethanol in 2 times while 1.5 hours for each time to obtain an extracted solution, merging the extracted solution, concentrating till no alcohol taste, obtaining an extractum for future use;

S2, dissolving the extractum after concentration obtained in the step S1 with 6 L of water, eluting the dissolved extractum by D101 macroporous adsorption resin column, with an eluent being ethanol and water in a volume ratio of 10:90 for three column volumes, collecting an eluate, naming the eluate as MM-1, for future use;

S3, eluting a fraction MM-1 collected in the step S2 by a reverse phase material ODS column chromatography, with an eluent being the ethanol-water system in a volume ratio of 28:72, eluting for 18 column volumes, collecting one fraction of eluate per three column volumes, thereby collecting 6 fractions in order, naming the 6 fractions as MM-11, MM-12, MM-13, MM-14, MM-15, MM-16 respectively, for future use;

S4, separating the fraction MM-12 collected in the step S3 by a preparative liquid phase, with a chromatographic column for the preparative liquid phase being YMC of 20 mm*250 mm with a velocity of 10 ml/min, a mobile phase being a methanol-water-acetic acid system, and a volume ratio of methanol-water-acetic acid being 10:90:0.01, collecting eluates in peak-order, collecting 7 fractions in total, naming the 7 fractions as MM-121, MM-122, MM-123, MM-124, MM-125, MM-126, MM-127 respectively, for future use; and S5, purifying the fraction MM-125 collected in the step S4 by the preparative liquid phase, with a chromatographic column for the preparative liquid phase being YMC of 20 mm*250 mm with a velocity of 5 ml/min, a mobile phase being the methanol-water-acetic acid system, and a volume ratio of methanol-water-acetic acid being 15:85:0.01, collecting an eluate, obtaining the phenylpropanoid compound after recrystallizing.

The compounds obtained from Examples 1 to 5 were carried out tests of MS, H-NMR and C-NMR. The results verify that the obtained compounds are 3',5'-dihydroxy-4'-glucosyl-phenyl-3-hydroxypropanoic acid methyl ester, with a structural formula shown as formula (I):

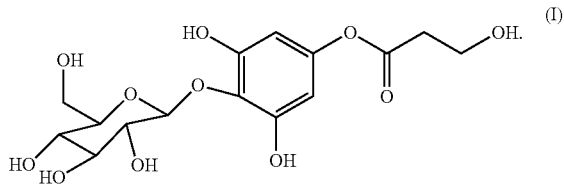 [SMILES: O=C(CCO)Oc1cc(O)c(OC2OC(CO)C(O)C(O)C2O)c(O)c1]

Spectrogram data of MS, H-NMR and C-NMR thereof is as follows:

HR-ESIMS shows [M+Na]+ as m/z 399.1889, and in combination with nuclear magnetic characteristics, a molecular formula was obtained as $C_{15}H_{20}O_{11}$ with an unsaturation degree being 6.

$^1$H-NMR (600 MHz, $CD_3OD$): 6.60 (d, 1H), 6.47 (d, 1H), 4.95 (s, 1H), 4.94 (m, 2H), 3.00-4.00 (glc-H), 2.71 (m, 2H).

$^{13}$C-NMR (150 MHz, $CD_3OD$): 170.5 (C-1), 150.7 (C-1'), 150.2 (C-4'), 135.5 (C-3',5'), 114.7 (C-2',6'), 101.2 (C-1"), 61.5-77.8 (C2"-C6"), 61.1 (C-2), 38.69 (C-3).

Example 6

Preparation of a Salt of a the Phenylpropanoid Compound
Preparation of Hydrochlorides of the Phenylpropanoid Compound:

Under stirring, a methanol solution of the compound was dripped with saturated hydrochloric acid to reach a pH value of 2 to 3, and then added with acetonitrile. White powder solid was obtained by filtration and drying, that is, hydrochloric acid salt of the compound.

Preparation of Sulfonates of the Phenylpropanoid Compound:

Alkali metal hydroxides, solvent, sulfuric acid, neutral oil, and accelerator were added to a reaction system containing the phenylpropanoid compound. Solvent, lower alcohol, and accelerator, and carbon dioxide were introduced into the reaction system to separate the white powder solid, i.e. sulfonates of the compound.

Preparation of Potassium or Sodium Salts of the Phenylpropanoid Compound:

Under stirring, KOH or NaOH dissolved in ethanol was added to the compound, heated to reflux under stirring, cooled to room temperature, dripped with acetonitrile, and then filtered and dried to white solid, i.e. potassium or sodium salt of the compound.

Preparation of Ammonium Salts of the Phenylpropanoid Compound:

Under stirring, the compound in methanol solution was dripped with saturated ammonia to reach a pH value of 9 to 11, stirred with acetonitrile, and then filtered and dried to white solid, i.e. ammonium salts of the phenylpropanoid compound.

Spectrogram Data of the Salt of the Compound Mentioned Above:

The hydrochlorides of the phenylpropanoid compound: ESIMS displays m/z 412.67, $^1$H-NMR (600 MHz, CD$_3$OD): 6.60 (s, 2H), 6.47 (m, 1H), 5.48 (s, 1H), 5.35 (s, 1H), 4.88 to 4.95 (m, 3H), 4.41 (s, 1H), 3.33 to 3.50 (m, 6H), 2.89 (s, 1H), 2.70 (m, 2H), 1.24 (m, 2H).

Potassium or Sodium Salts of the Phenylpropanoid Compound:

The potassium salts of the phenylpropanoid compound: ESIMS displays m/z 452.19, $^1$H-NMR (600 MHz, CD$_3$OD): 6.62 (s, 2H), 4.86 to 4.97 (m, 3H), 4.42 (s, 1H), 3.33 to 3.51 (m, 6H), 2.90 (s, 1H), 2.71 (m, 2H), 1.24 (m, 2H).

The sodium salts of the phenylpropanoid compound: ESIMS displays m/z 420.06, $^1$H-NMR (600 MHz, CD$_3$OD): 6.62 (s, 2H), 6.47 (m, 1H), 4.86 to 4.97 (m, 3H), 4.42 (s, 1H), 3.33 to 3.51 (m, 6H), 2.90 (s, 1H), 2.71 (m, 2H), 1.24 (m, 2H).

Ammonium salts of the phenylpropanoid compound: ESIMS displays m/z 410.15, $^1$H-NMR (600 MHz, CD$_3$OD): 6.60 (s, 2H), 6.47 (m, 1H), 5.48 (s, 1H), 5.35 (s, 1H), 4.88 to 4.95 (m, 3H), 4.41 (s, 1H), 3.33 to 3.50 (m, 6H), 2.89 (s, 1H), 2.70 (m, 2H), 1.24 (m, 2H).

The structural formula of the phenylpropanoid compounds mentioned above is shown in Formulas (III) to (VII).

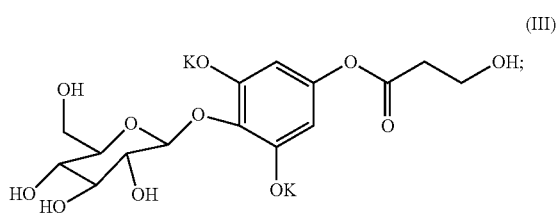

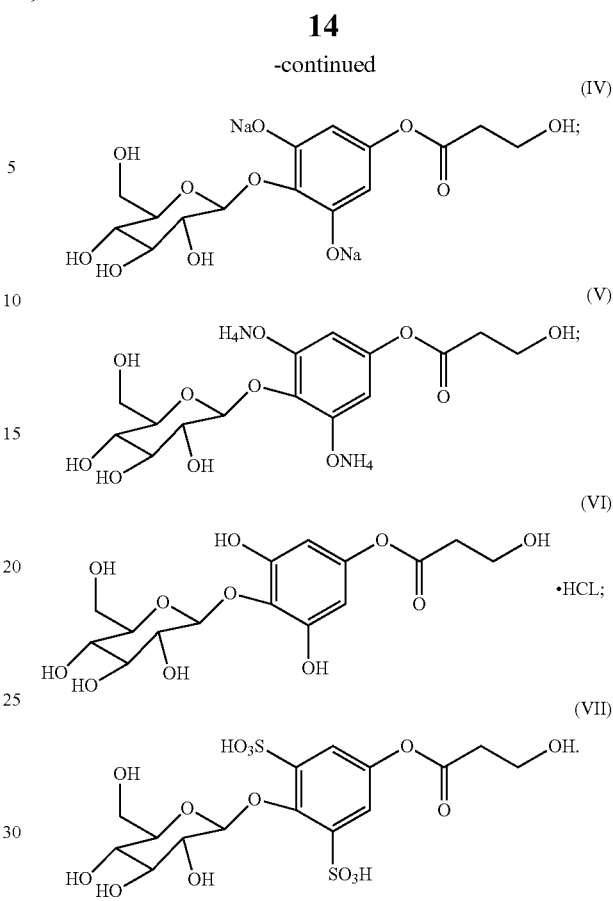

Wherein, Formula (III) is one of the prepared potassium salts of the phenylpropanoid compound, Formula (IV) is one of the prepared sodium salts of the phenylpropanoid compound, Formula (V) is one of the ammonium salts of the phenylpropanoid compound, Formula (VI) is the hydrochloride of the phenylpropanoid compound, and Formula (VII) is one of the sulfonates of the phenylpropanoid compound.

Example 7

Application Experiments

The compound and salts of present invention have effects on LPS-induced oxidative stress and inflammation of RAW 264.7 macrophages. (For convenience of recording during experiment, the phenylpropanoid compound described in present invention is labelled as: MM-125, that is, MM-125 described in present invention refers to the phenylpropanoid compound shown in formula (I) of present invention or their pharmaceutically acceptable salts.)

1 Materials and Methods
1.1 Medicine and Devices

Lipopolysaccharide (LPS), MTT purchased from Sigma, Raw 264.7 mouse macrophage purchased from Xiangya cell bank; PBS; DMEM high glucose medium, fetal bovine serum, penicillin and streptomycin, automatic enzyme labelling instrument, constant temperature CO$_2$ incubator.

Mouse IL-1-beta ELISA kit, batch number: 2014/06 (96T), Mouse IL-6 ELISA kit, batch number: 2014/06 (96T), Mouse tumor necrosis factor-alpha (TNF-α) ELISA kit, batch number: 2014/06 (96T), Mouse NO ELISA Kit Batch number: 2014/10 (96T), mouse hydroxyl radical (OH) ELISA detection kit, batch number: 2014/10 (96T).

1.2 Preparation of Medicine

Medicine was first dissolved in a small amount of DMSO, and then diluted to a certain concentration with DMEM, so that final concentration of DMSO was less than 1%.

1.3 Cell Culture

Raw 264.7 mouse macrophages were incubated in DMEM medium containing 10% heat-inactivated fetal bovine serum (FBS), 10 U/mL penicillin sodium and 100 μg/ml streptomycin, and incubated in 37° C., 5% $CO_2$ incubator.

1.4 Determination of Cell Vitality

Cell vitality was determined by MTT method. Cell suspension liquid was inoculated into a 96-well plate (1*104 holes/pore) to incubate for 24 hours and then synchronize for 24 hours. The cells were treated with different concentration of medicine for 2 hours, and then stimulated by LPS (30 μg/ml) for 24 hours. Original medium was abandoned, and MTT (0.5 mg/ml) was added into each hole for 4 hours. The medium was then abandoned and DMSO (150 μg/ml) was added into each hole. Absorbance was measured at 490 nm after shaking for 10 min.

1.5 Determination of NO Concentration

Raw 264.7 cells were inoculated on a 96-well plate for 24 hours, then synchronized for 24 hours. The cells were treated with different concentration of medicine for 2 hours, and then stimulated with LPS (30 μg/ml) for 24 hours. Lastly, supernatant was collected and centrifuged for 5 minutes at 10,000 rpm. The supernatant was separated and stored at −80° C. for reserve. The concentration of NO was determined by mouse NO kit.

1.6 Measurement of Inflammatory Factors TNF-α, IL-1β, IL-6

Sample prepared in at 1.5 was used for subsequent inflammatory factor determination. The amount of TNF-α, IL-1β, IL-6 produced by cells was measured by mouse TNF-α, IL-1β, and IL-6 kit.

1.7 Determination of OH Concentration

Sample prepared at 1.5 was used for OH factor determination. The concentration was determined by OH kit.

1.8 Statistical Analysis

SPSS17.0 software was used, and experiment data was expressed as x±s. The data obtained was analysed by one-way ANOVA. Homogeneity of variance is tested by LSD, and Dunnett T3 was used for variant homogeneity.

2 Experimental Results 2.1 Cell Vitality

The effect of medicine on cell vitality was evaluated by MTT method. As shown in FIG. 1, MM-125 had no significant effect on vitality of Raw 264.7 cells in a range of 1.37 to 12.37 μg/ml. Therefore, concentration of MM-125 in this range was suitable for subsequent experiments.

2.2 Medicine Inhibits NO Production

Figure 2:
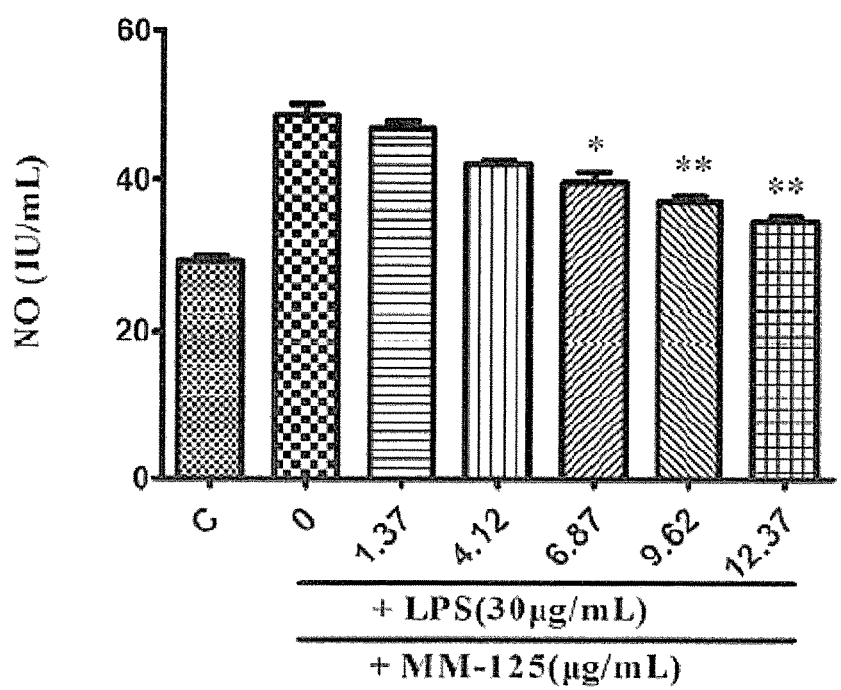
FIG. 2 shows an inhibition effect diagram of the phenylpropanoid compound of the present invention on NO.

As shown in FIG. 2, NO production (48.66±1.66 IU/mL) of Raw 264.7 cells stimulated by LPS was significantly higher ($p<0.01$) than that of normal Raw 264.7 cells (29.05±0.85 IU/ml). In a range of 6.88±12.38 μg/ml, MM-125 could significantly inhibit the increase of NO concentration induced by LPS in a dose-dependent manner.

2.3 Medicine Inhibits Production of TNF-α, IL-1β, and IL-6

Figure 3:
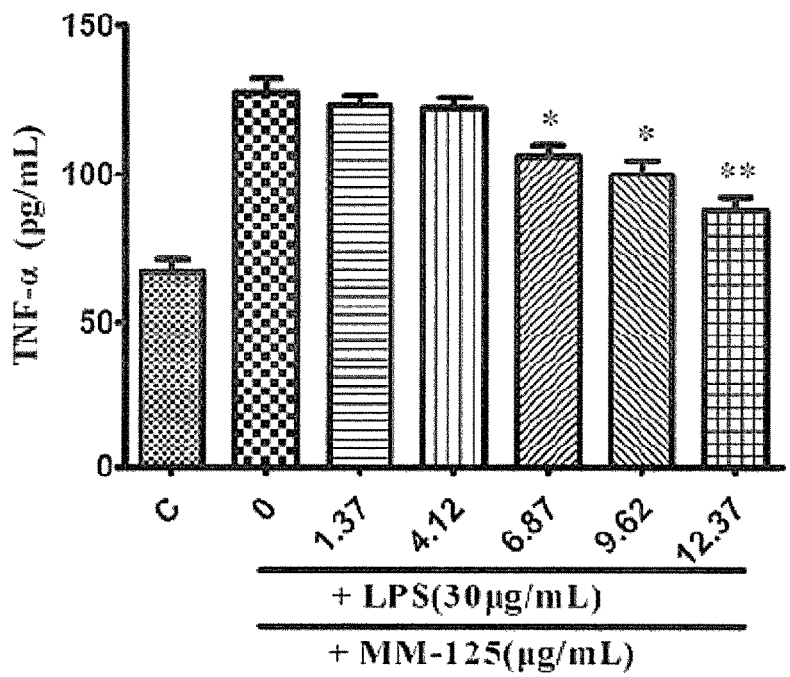
FIG. 3 shows an inhibition effect diagram of the phenylpropanoid compound of the present invention on TNF-α.
Figure 4:
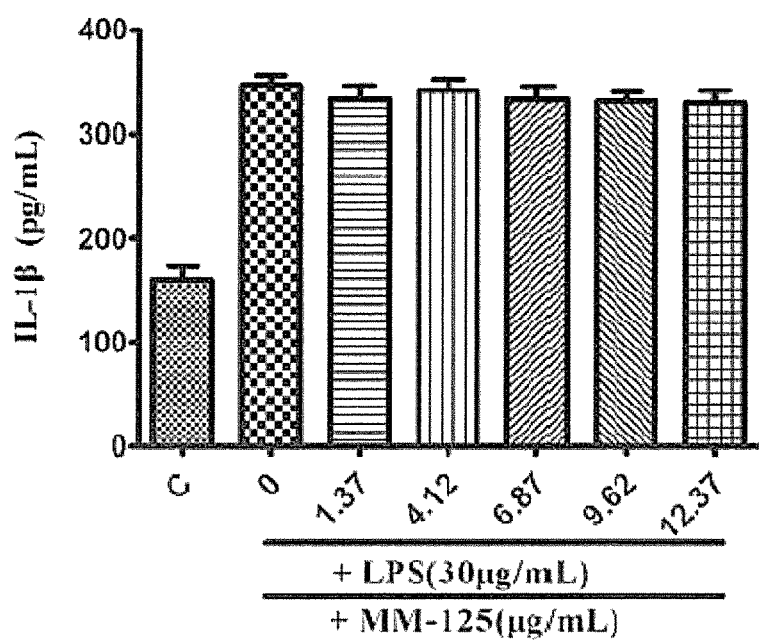
FIG. 4 shows an inhibition effect diagram of the phenylpropanoid compound of the present invention on IL-1β.
Figure 5:
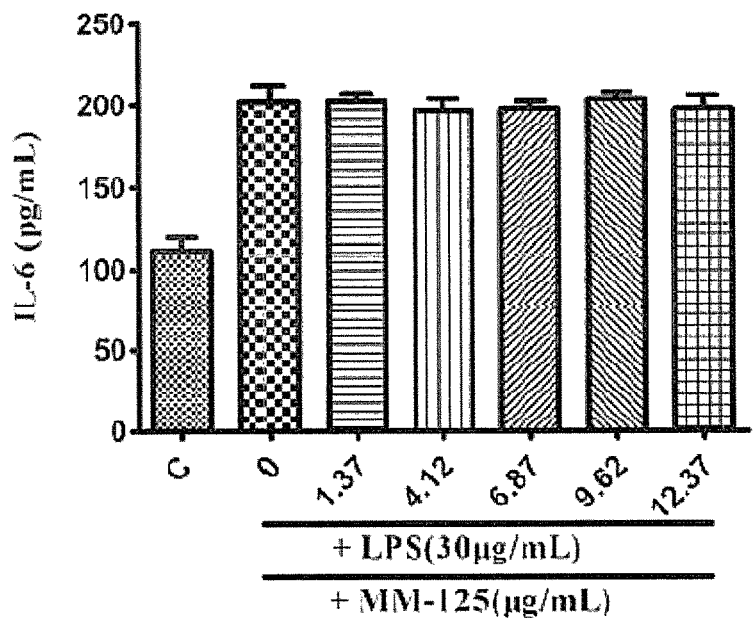
FIG. 5 shows an inhibition effect diagram of the phenylpropanoid compound of the present invention on IL-6.

As shown in FIGS. 3 to 5, concentrations of inflammatory cytokines TNF-α (127.98±4.65 pg/ml), IL-1β (347.55±9.56 pg/ml), and IL-6 (201.67±10.32 pg/ml) were significantly higher than those in normal controls ($p<0.01$): TNF-α (67.12±4.00 pg/ml), IL-1β (160.88113.10 pg/ml), and IL-6 (111.13±8.06 pg/ml), which indicates that LPS could stimulate Raw 264.7 cells to produce a large number of inflammatory factors.

In a range of 6.88±12.38 μg/ml, MM-125 could significantly inhibit production of TNF-α ($p<0.05$) in Raw 264.7 cells in a dose-dependent manner, but could not inhibit production of IL-1β or IL-6 ($p>0.05$) at various concentrations.

2.4 Medicine Inhibits OH Production

Figure 6:
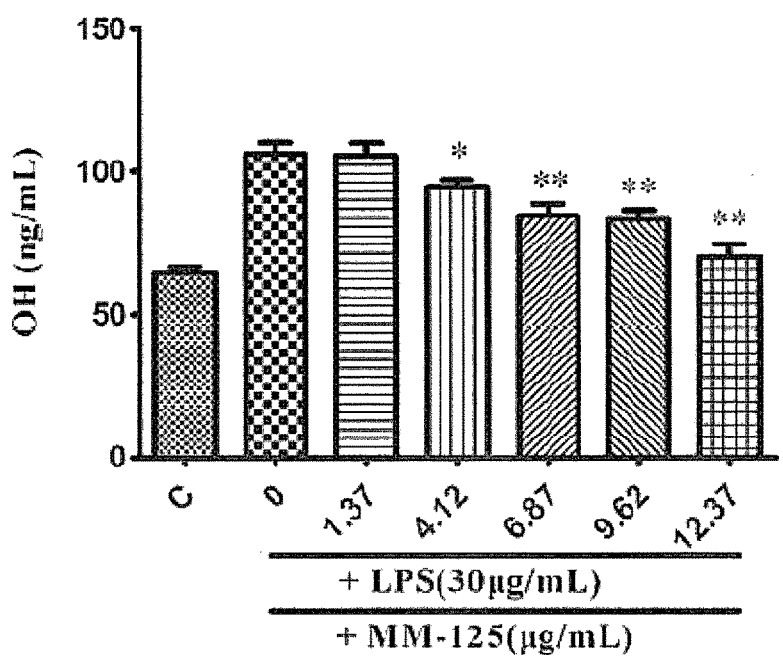
FIG. 6 shows an inhibition effect diagram of the phenylpropanoid compound of the present invention on OH.

As shown in FIG. 6, Raw 264.7 cells stimulated by LPS produced higher OH concentration (106.00±3.90 ng/ml) than normal controls (64.62±2.18 ng/ml). ($p<0.01$)

In a range of 4.13-12.38 μg/ml, MM-125 could significantly inhibit the increase of OH concentration induced by LPS in a dose-dependent manner.

Effects of MM-125 on production of NO, TNF-α, IL-1β, IL-6, and OH in mouse macrophages were studied in vitro.

MM-125 has significant inhibitory effects on production of cytokine NO and also certain level of inhibiting effects on TNF-alpha, but it has no obvious inhibitory effect on IL-1β or IL-6, indicating that MM-125 has certain anti-inflammatory capability. It has significant inhibitory effects on production of OH, indicating that it has better antioxidant capability.

Example 8

Preparation of tablets: the phenylpropanoid compound shown in Formula (I) was prepared according to the method in Example 1, using salts made of the compound with inorganic acids (e.g. hydrochloric acid, hydrobromic acid, hydrofluoric acid, hydroiodic acid, sulfuric acid, nitric acid, carboxylic acid, phosphoric acid, lactic acid) or sulfonic acid or hydroxide salts of alkali metals (e.g. potassium hydroxide, sodium hydroxide, calcium hydroxide, magnesium hydroxide, lithium hydroxide) or ammonium. Tablets are pelleted and tableted by adding excipients in a proportion of 1:10 weight ratio (of the compound or any of its salts to the excipient).

Example 9

Preparation of powder: the phenylpropanoid compound shown in Formula (I) was prepared according to the method in Example 1, using salts made of the compound with inorganic acids (e.g. hydrochloric acid, hydrobromic acid, hydrofluoric acid, hydroiodic acid, sulfuric acid, nitric acid, carboxylic acid, phosphoric acid, lactic acid) or sulfonic acid or hydroxide salts of alkali metals (e.g. potassium hydroxide, sodium hydroxide, calcium hydroxide, magnesium hydroxide, lithium hydroxide) or ammonium. The compound or its salts was made into powder using conventional methods.

Example 10

Preparation of capsules or granules: the phenylpropanoid compound shown in Formula (I) was prepared according to the method in Example 1, using salts made of the compound with inorganic acids (e.g. hydrochloric acid, hydrobromic acid, hydrofluoric acid, hydroiodic acid, sulfuric acid, nitric acid, carboxylic acid, phosphoric acid, lactic acid) or sulfonic acid or hydroxide salts of alkali metals (e.g. potassium hydroxide, sodium hydroxide, calcium hydroxide, magnesium hydroxide, lithium hydroxide) or ammonium. Excipients were added to the compound or any of its salts in a weight ratio of 1:10 (of the compound or any of its salts to the excipient) to make capsules or granules.

Example 11

Preparation of injections: the phenylpropanoid compound shown in Formula (I) was prepared according to the method in Example 1, using salts made of the compound with inorganic acids (e.g. hydrochloric acid, hydrobromic acid, hydrofluoric acid, hydroiodic acid, sulfuric acid, nitric acid, carboxylic acid, phosphoric acid, lactic acid) or sulfonic acid or hydroxide salts of alkali metals (e.g. potassium hydroxide, sodium hydroxide, calcium hydroxide, magnesium hydroxide, lithium hydroxide) or ammonium. Injection was made by conventional water injection, fine filtration, encapsulation and sterilization.

Example 12

A pharmaceutical composition, containing a phenylpropanoid compound shown in Formula (I) prepared according to the method in Example 1, and salts made of the compound with inorganic acids (e.g. hydrochloric acid, hydrobromic acid, hydrofluoric acid, hydroiodic acid, sulfuric acid, nitric acid, carboxylic acid, phosphoric acid, lactic acid) or sulfonic acid or hydroxide salts of alkali metals (e.g. potassium hydroxide, sodium hydroxide, calcium hydroxide, magnesium hydroxide, lithium hydroxide) or ammonium, and powder made of Radix *Rosa Laevigata, Zanthoxylum dissitum* Hemsl., *Caulis Spatholobi, Caulis Mahoniae, Herba Andrographis*, Radix *Angelicae Sinensis*, Radix *Codonopsis*, and supplementary materials.

Example 13

A pharmaceutical composition, containing a phenylpropanoid compound shown in Formula (I) prepared according to the method in Example 1, and powder made of Radix *Rosa Laevigata, Zanthoxylum dissitum* Hemsl., *Caulis Spatholobi, Caulis Mahoniae, Herba Andrographis*, Radix *Angelicae Sinensis*, Radix *Codonopsis*, and supplementary materials.

Example 14

A pharmaceutical composition, containing a phenylpropanoid compound shown in Formula (I) prepared according to the method in Example 1, and extracts of Radix *Rosa Laevigata, Zanthoxylum dissitum* Hemsl., *Caulis Spatholobi, Caulis Mahoniae, Herba Andrographis*, Radix *Angelicae Sinensis*, Radix *Codonopsis*, and supplementary materials. The extract was prepared according to methods described in one or more patent documents among CN1078079C, CN1170549C, CN1158087C, CN1330335C, CN1296071C, CN1321631C, CN1296072C, CN1296073C.

Example 15

A pharmaceutical composition, containing a phenylpropanoid compound shown in Formula (I) prepared according to the method in Example 1, and salts made of the compound with inorganic acids (e.g. hydrochloric acid, hydrobromic acid, hydrofluoric acid, hydroiodic acid, sulfuric acid, nitric acid, carboxylic acid, phosphoric acid, lactic acid) or sulfonic acid or hydroxide salts of alkali metals (e.g. potassium hydroxide, sodium hydroxide, calcium hydroxide, magnesium hydroxide, lithium hydroxide) or ammonium, and extracts of Radix *Rosa Laevigata, Zanthoxylum dissitum* Hemsl., *Caulis Spatholobi, Caulis Mahoniae, Herba Andrographis*, Radix *Angelicae Sinensis*, Radix *Codonopsis*, and supplementary materials. The extract was prepared according to methods described in one or more patent documents among CN1078079C, CN1170549C, CN1158087C, CN1330335C, CN1296071C, CN1321631C, CN1296072C, CN1296073C.

The above shows and describes basic principles and main features and advantages of present invention. It should be understood by those skilled in the art that present invention is not limited by embodiments and specifications mentioned above, which describe only the principles of present invention, and that present invention will undergo various changes and improvements without departing from the spirit and scope of present invention, which is obvious to those skilled in the art. These changes and improvements fall into the scope of the requirement to protect the invention. The invention requires that the scope of protection be defined by appended claims and their equivalents.

What is claimed is:

1. A pharmaceutically acceptable salt of a phenylpropanoid compound, wherein the pharmaceutically acceptable salt has a structural formula shown as formula (II), formula (III), formula (IV), or formula (V):

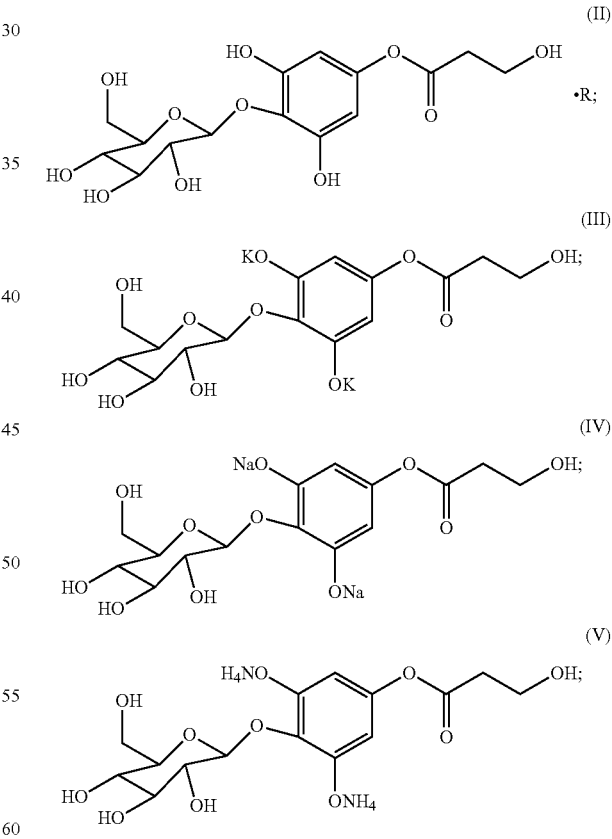

wherein the R is an inorganic acid.

2. The pharmaceutically acceptable salt of the phenylpropanoid compound according to claim 1, wherein the inorganic acid is selected from a group consisting of hydrochloric acid, hydrobromic acid, hydrofluoric acid, hydroiodic acid, sulfuric acid and phosphoric acid.

3. The pharmaceutically acceptable salt of the phenylpropanoid compound according to claim 1, wherein the pharmaceutically acceptable salt is an ammonium salt.

4. A pharmaceutical composition, wherein the pharmaceutical composition contains the pharmaceutically acceptable salt of the phenylpropanoid compound according to claim 1.

5. The pharmaceutical composition according to claim 4, wherein the pharmaceutical composition further contains a pharmaceutically permissible supplementary material and/or carrier.

6. The pharmaceutical composition according to claim 4, wherein the pharmaceutical composition further contains one or more of Radix *Rosa Laevigata, Zanthoxylum dissitum* Hemsl., *Caulis Spatholobi, Caulis Mahoniae, Herba Andrographis*, Radix *Angelicae Sinensis*, Radix *Codonopsis*, or an extract thereof.

7. The pharmaceutical composition according to claim 4, wherein the pharmaceutical composition has a form selected from a group consisting of a tablet, a capsule, a powder, a granule, a pill, a solution, a suspension, a syrup, an injection, an ointment, a suppository and a spray.

8. A preparation method of a phenylpropanoid compound, wherein the preparation method comprises steps as follows:
   S1, taking a root of *Moghania macrophylla* (Willd.) O. Kuntze as a raw material, drying, stripping and slicing, extracting with an ethanol solution to obtain an extracted solution, merging the extracted solution, concentrating till no alcohol taste, obtaining an extractum for future use;
   S2, dissolving the extractum obtained in the step S1 with water, eluting the dissolved extractum by a macroporous adsorption resin column, with an eluent being an ethanol-water system, collecting first three column volumes of an eluate, naming the eluate as MM-1, for future use;
   S3, eluting a fraction MM-1 collected in the step S2 by a reverse phase material ODS column chromatography, with an eluent being the ethanol-water system, eluting for 18 column volumes, collecting one fraction of eluate per three column volumes, thereby collecting 6 fractions in order, naming the 6 fractions as MM-11, MM-12, MM-13, MM-14, MM-15, MM-16 respectively, for future use;
   S4, separating the fraction MM-12 collected in the step S3 by a preparative liquid phase, with a mobile phase being a methanol-water-acetic acid system, collecting eluates in peak-order, collecting 7 fractions in total, naming the 7 fractions as MM-121, MM-122, MM-123, MM-124, MM-125, MM-126, MM-127 respectively, for future use; and
   S5, purifying the fraction MM-125 collected in the step S4 by the preparative liquid phase, with a mobile phase being the methanol-water-acetic acid system, collecting an eluate, obtaining the phenylpropanoid compound after recrystallizing, wherein the phenylpropanoid compound has a structural formula shown as formula (I):

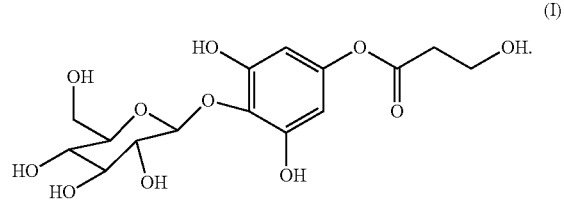 [SMILES: O=C(CCO)Oc1cc(O)c(OC2OC(CO)C(O)C(O)C2O)c(O)c1]

9. The preparation method according to claim 8, wherein in the step S1, a concentration of the ethanol solution is 50 to 80% by volume.

10. The preparation method according to claim 8, wherein in the step S1, extracting with ethanol performs 2 to 4 times, and each time is 1 to 3 hours.

11. The preparation method according to claim 8, wherein in the step S2, a volume ratio of ethanol to water is 0:100 to 15:85.

12. The preparation method according to claim 8, wherein in the step S3, for the eluent, a volume ratio of methanol to water is 20:80 to 30:70.

13. The preparation method according to claim 8, wherein in the step S4, a volume ratio of methanol to water to acetic acid is 10:90:0.01 to 35:65:0.01.

14. The preparation method according to claim 8, wherein in the step S4 and/or the step S5, a chromatographic column of the preparative liquid phase is YMC, 20 mm*250 mm, and a flow rate of the mobile phase is 5 to 10 mL/min.

15. The preparation method according to claim 8, wherein in the step S5, a volume ratio of methanol to water to acetic acid is 15:85:0.01.

16. A method of using a phenylpropanoid compound and a pharmaceutically acceptable salt thereof for treating an inflammatory disease, the method comprises:
   preparing a medicine by using the phenylpropanoid compound or the pharmaceutically acceptable salt thereof, wherein the phenylpropanoid compound has a structural formula shown as formula (I), and the pharmaceutically acceptable salt has a structural formula shown as formula (II), formula (III), formula (IV), or formula (V):

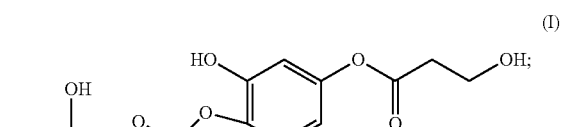

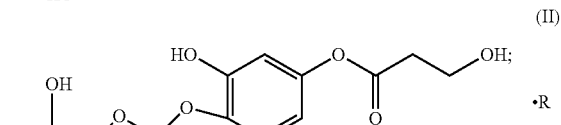

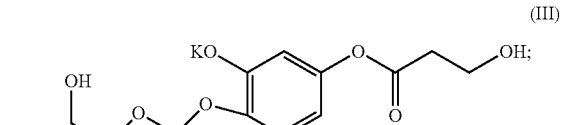

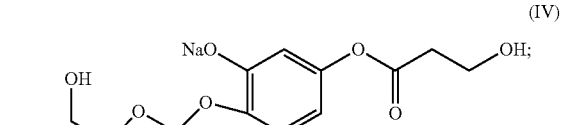

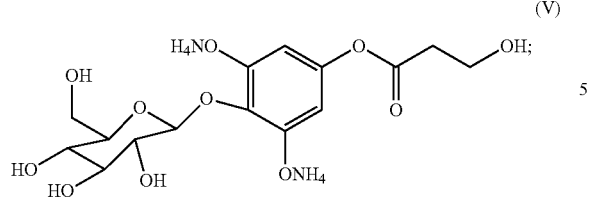

wherein the R is an inorganic acid; and
administering the medicine for treating the inflammatory disease.

17. The method according to claim 16, wherein the medicine is for inhibiting a content of an inflammatory cytokine NO or inhibiting an expression of an inflammatory cytokine TNF-α or inhibiting an activity of a hydroxyl radical.

18. The method according to claim 16, wherein the inflammatory disease is cervicitis, endometritis, pelvic inflammatory disease, mastitis, sphagitis and/or arthritis.

19. The method according to claim 16, wherein the medicine contains a pharmaceutically permissible supplementary material and/or carrier.

20. The method according to claim 16, wherein the medicine further contains one or more of Radix *Rosa Laevigata, Zanthoxylum dissitum* Hemsl., *Caulis Spatholobi, Caulis Mahoniae, Herba Andrographis*, Radix *Angelicae Sinensis*, Radix *Codonopsis*, or an extract thereof.

* * * * *